United States Patent [19]

Lau

[11] Patent Number: 5,690,956
[45] Date of Patent: Nov. 25, 1997

[54] HAIR CARE PERMING AGENT

[75] Inventor: John R. Lau, Howard, Ohio

[73] Assignee: SDG, Inc., Wooster, Ohio

[21] Appl. No.: 534,296

[22] Filed: Sep. 27, 1995

[51] Int. Cl.$^6$ ........................................ A61K 9/127
[52] U.S. Cl. .............................. 424/450; 424/70.2
[58] Field of Search ....................... 424/450, 70.2

[56] References Cited

U.S. PATENT DOCUMENTS 4,145,305   3/1979   Démarcq .................. 252/186

FOREIGN PATENT DOCUMENTS 639015   4/1964   Belgium .................. 424/70.2

*Primary Examiner*—Thurman K. Page
*Assistant Examiner*—Murthy Sikha
*Attorney, Agent, or Firm*—Fay, Sharpe, Beall, Fagan, Minnich & McKee

[57] ABSTRACT

Strong reducing chemicals are required by prior art to break disulfide bonds of hair structure in alkaline media. The disulfide bonds are responsible for holding the hair in set condition.

This disclosure teaches a new means for breaking the disulfide bonds by use of Tris-(2-carboxyethyl) phosphine (TCEP) in a mildly acid solution.

The essence of the specification is the breaking of disulfide bonds in an acid environment.

6 Claims, No Drawings

HAIR CARE PERMING AGENT

BACKGROUND OF THE INVENTION

1. Field of the Invention

Hair perming and straightening.

2. Information Disclosure Statement

This invention is an outstanding discovery of hair perming, and therefore will be directed primarily to the hair perming industry.

There are volumes of reports on the prior art effort to change the physical structure of hair. One example is *THE SCIENCE OF HAIR CARE*, Marcel Dekker, Inc, New York, N.Y. @1986.

There is no pertinent prior art known to applicant other than the practice of hair salon techniques, and the text book by Dekker.

At the present time, the method of choice is to use mechanical devices to form hair around tubular rollers, and use alkaline based sulfhydryl chemical reducing agents to disrupt the hair disulfide bonds. The hair is then flexible and able to set in a new configuration.

It is possible to change the hair structure without mechanical devices, but the bulk of hair perming is done either to straighten hair or produce hair that is styled with curls and waves. The perming of hair will be the primary teaching disclosure of this specification.

The chemical reaction for the sulfhydryl based system is shown below:

Prior Art Hair Perming Sulfhydryl Chemistry

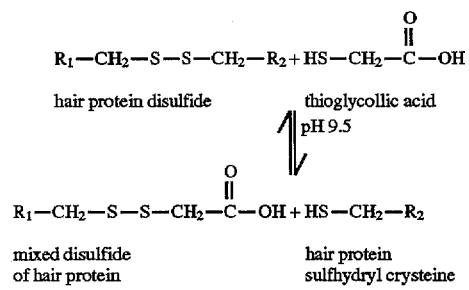

$R_1-CH_2-S-S-CH_2-R_2 + HS-CH_2-C(=O)-OH$ hair protein disulfide     thioglycollic acid pH 9.5

$R_1-CH_2-S-S-CH_2-C(=O)-OH + HS-CH_2-R_2$ mixed disulfide of hair protein     hair protein sulfhydryl crysteine The disulfide bond ($R_1-S-S-R_2$) in hair protein is reacted on by a chemical reducing agent containing a free sulfhydryl functional group, such as thioglycollic acid. As a result of the above reaction, two essential products are formed. The first product is a mixed disulfide compound containing a component of hair protein and a component of thioglycollic acid. The second product is formed as a result of the cleavage of the original disulfide bond. Half of this original bond is now manifested as a free sulfhydryl compound capable of engaging in further reaction toward any disulfide linkage.

Thioglycollic acid is effective, but unpleasant and sometimes harmful to use. Because it functions in an alkaline environment, it must be used in a careful manner to prevent eye damage and skin irritation. The odor of the perming reaction can be offensive and the time for completion of the procedure is often tiring to the recipients. Thioglycollic acid is used at elevated pH usually between pH 9–12. The harsh alkaline environment leads to severe cuticle damage. This results in hair that is brittle and has an abrasive or rough texture.

Naturally curly hair can be straightened during combing by first applying a reducing agent which reacts with the disulfide bonds. Also, if only partial straightening is desired, tight curly hair may be made straight using milder reducing conditions. It is recognized that hair strands, whether straight or curly, are held in a given physical configuration by disulfide bonds. It has long been practiced to shape straight hair by physically stressing the hair shaft. Thus, by wrapping the hair around curlers the hair will take on a new configuration. This procedure takes a considerable amount of time, and is very responsive to humidity.

Human hair has chemical and physical properties which makes it both strong and elastic. A key structural component of hair is a molecule of cystine created by two cysteine moieties joined by a disulfide bond. This structure of cysteine is depicted as ($R_1-S-S-R_2$). The abbreviations $R_1$ and $R_2$ are representative of hair protein strands connected by a disulfide bond.

It has also been recognized that using strong reducing agents, such as thioglycollic acid in the presence of sodium hydroxide in a pH range from pH 9 to 11 and even higher, will cause hair to become pliable and easily formed into a new configuration. The thioglycollic acid is effective in disrupting the disulfide bond, but poses a risk to human health because of the strong basic conditions that are required to drive the reaction. These conditions increase the possibility of injury to the hair, as well as to the skin and eyes of the user.

Any process for changing the hair shaft must depend on softening or plasticizing the three dimensional structure of the hair protein. Therefore, it is the practice of hair perming techniques to reshape the hair in a desired style while it is soft and manageable, then harden or set the hair, thus enabling the hair to hold its new shape.

It is therefore an object of this invention to provide a useful, safe, and efficient means of disrupting the disulfide bonds in hair while in a mildly acidic environment, which leads to the successful practice of hair perming.

Another object of this invention is to provide a reducing agent Which creates reaction products that when formed in a mildly acidic environment lacks significant reactivity toward each other, thus enabling the reaction to be under kinetic control.

A further object of this invention is to avoid the use of strong reducing chemicals requiring high pH for activity and provide instead, a mildly acidic medium in which the reducing agent can engage in the necessary chemical reactions that lead to significantly improved hair perming, better hair styling and better overall hair care.

A further object of this invention is to deliver a substrate, which will promote an oxidation of sulfhydryl functional groups to disulfide bonds, without having to remove or wash away the reducing agent.

SUMMARY OF THE INVENTION

Previous to this invention, Tris-(2-carboxyethyl) phosphine (TCEP), a known reducing agent, was found to function well on soluble proteins, such as antibodies, in the presence of 6M guanidine or 8M urea.

By contrast, TCEP can be used, according to the discovery of this invention, as the sole reactive agent to break disulfide bonds within an insoluble substrate, namely hair, thus initiating the reducing sequence leading to the practice of permanent hair waving.

In addition, this discovery entails the recognition that TCEP is an exceptionally safe reducing agent. When TCEP operates in a mildly acidic environment, not practiced by the prior art in permanent hair waving, it provides kinetic control of the reducing reaction parameters by breaking disulfide bonds in hair shafts to form free sulfhydryl functional groups which are unreactive at mildly acidic pH. The observation that disulfide bonds are normally buried and sequestered within the hair shaft suggests that they are unavailable for participation in reactions involving simple solution chemistry. This fact supports the discovery that TCEP is unique and effective in hair perming practice because it can penetrate the hair shaft and react with disulfide bonds at mildly acidic pH.

BEST MODE—PREFERRED EMBODIMENT

Historically, in hair waving practices, the reducing agents have been thiol based compounds, such as thioglycollate and have found favor with consumers, hair salons, and hair perming industries. This invention is in the recognition of the advantages of disrupting the disulfide bonds in hair protein by a reducing agent that is active in an acidic environment. This obviates the need to use harsh alkaline conditions practiced by the prior art.

The extent of cleavage of disulfide bonds using thioglycollate depends on the concentration of the reducing agent and on the amount of mechanical stress applied to the hair shaft. In spite of the conditions used in performing a reduction of the disulfide bonds, in prior practice in a laboratory setting, no more than 65–70% of the protein cystine bonds in hair were disrupted. In the actual practice of hair perming, the reduction level is even lower, ranging between 19% and 43%. When using thioglycollate as a reducing agent, the optimal perming condition occurs using ambient temperatures and a 5% (w/v) solution of thioglycollate.

It is recognized that the pKa of the particular thiol compound that is selected as a reducing agent is important since it can determine in part the rate at which chemical equilibrium of the reducing reaction is reached.

Once the disulfide bonds in hair have been reduced, the re-oxidation of these bonds is a necessary and prerequisite step in order to cross-link or set the proteinaceous structure of hair into a desired form. The basic process is simple re-oxidation of the sulfhydryl cysteine moieties into disulfide cystine molecules. This reaction lends stability to the structural fibril components of hair and restores some of the former chemical and physical properties exhibited by hair prior to reduction.

This invention addresses permanent waving of hair by utilizing a reducing agent known chemically as Tris-(2-carboxy-ethyl) phosphine hydrochloride (TCEP-HCL), hereinafter, referred to by the acronym TCEP. TCEP is more effective than traditional sulfhydryl reducing agents, such as dithiothreitol, mercaptoethanol, or thioglycollic acid in reducing disulfide bonds at acidic pH and does not have the mal-odor or the autoxidation problems that are typically associated with these other agents.

The reducing agent TCEP of this disclosure is water soluble, odorless and colorless. TCEP is stable in aqueous acidic media and is therefore capable of exhibiting pronounced shelf-life stability. The chemical specificity of TCEP compounds permits reduction of disulfide bonds of the general type ($R_1$—S—S—$R_2$) and is essentially non-reactive toward other functional groups found in hair. The objections set forth in the prior art have been overcome by the concept of this invention. The molecule of TCEP shown below is carboxyethylated at three positions on the phosphorous atom thus leading to enhanced hydrophilicity and water solubility.

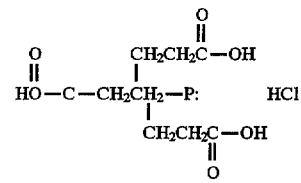

Tris-(2-carboxyethyl) phosphine hydrochloride
TCEP

Some of the advantages noted in using Tris-(2-carboxyethyl) phosphine.HCL to reduce the disulfide bonds in hair include:

1) Selective and complete reduction of some of the most stable disulfide bonds.

2) The reducing reactions are conducted under conditions of ambient or slightly elevated temperature in a mildly acidic buffer media ranging in a pH from 2.0–5.6 and with a TCEP concentration range of 5–10% w/v. The reaction occurs over a period of about 15 minutes.

3) A high water solubility of TCEP approaching 310 grams per liter promotes easy removal of TCEP from hair by water rinsing.

4) TCEP has properties which render it odorless and non-volatile leading to an enhanced consumer acceptance and safety.

5) TCEP is substantially resistant to air oxidation providing better product quality control characteristics.

6) TCEP has a very favorable safety profile and is not toxic to human hosts.

7) TCEP results in a lower instance of damaged hair, especially the cuticle. Pronounced damage to hair is caused by other reducing agents that rely upon sulfhydryl chemistry in alkaline pH environments.

8) TCEP participates in reaction conditions which are kinetically controlled.

Because of the chemical properties of Tris-(2-carboxyethyl) phosphine, reduction of disulfide bonds in hair protein is exceptionally efficient without the mal-odor that ordinarily accompanies sulfhydryl reducing agents. In addition, TCEP is also very stable when exposed to fluctuations in temperature. As a result, TCEP demonstrates a unique and favorable advantage over the prior art.

No extensive alteration in the hair perming procedure is required. The structural form of the hair shaft is firm until the disulfide bond in hair protein is disrupted by a reducing agent. Once reduced, the hair becomes softened and while on hair curlers, is formed to the desired and ultimate configuration.

Since TCEP is a much more effective reducing agent at mildly acidic pH than sulfhydryl compounds, a different and more pronounced pattern of disulfide bond breakage occurs. TCEP functions mechanistically by employing a kinetically controlled reaction. As a result, when disulfide bonds are broken, only free sulfhydryl groups are produced. These functional groups are not chemically reactive because the ionization of the sulfhydryl group has been suppressed by the low pH. Thus, the sulfhydryl groups are not permitted to cross react with themselves. These conditions then allow the oxidation of TCEP to proceed to completion in an irreversible manner. Subsequently, when an oxidizing agent is applied to the hair shaft, a substantial new rearrangement of disulfide bonds is created imparting the desired wave characteristic and styling to the hair.

Setting of Hair Shaft in New Form

Once the disulfide bonds have been broken, and the hair placed in stress to establish the final style which may be either straight, wavy, or curly, the disulfide bonds must then be re-established. Oxidation to restore the reduced bond can be obtained by simply exposing the hair to atmospheric oxygen, but this oxidation step is so very slow as to be of little practical use.

Present day practice is to use any one of a variety of oxidizing agents, but it is generally preferable to use hydrogen peroxide at a concentration of approximately 3% w/v.

Before applying hydrogen peroxide, it is necessary, according to prior art practice, to thoroughly rinse away the thioglycollic acid or other sulfhydryl reducing agent, otherwise, the remaining reducing agent will react with protein sulfhydryls thereby making them unavailable for establishing cross-links between adjacent protein chains. Consequently, in previous hair perming practice at elevated pH, prior to any oxidizing step, hair protein can engage in non-essential cross-linking. The result, if carried out on the hair of a client, would yield a poor hair set.

An exceptionally valuable portion of the present invention is manifest in that no rinsing of the TCEP is needed before using the oxidizing agent. There is no malodor, unsightly residue, or uncontrollable cross-linking of sulfhydryls.

Improved Resetting of Disulfide Bonds

In the standard version of the present invention, after the hair has been physically reformed, TCEP is then applied to the hair. TCEP will react with the disulfide bonds existing in hair and cause a reduction of these bonds, thereby, allowing the hair to become limp and workable.

Then, after the hair has been physically reformed and a short period of time (15 to 20 minutes) is allowed for completion of the bond breaking reaction, the oxidation process is then carried out on the previously reduced hair. This process will re-establish the disulfide bonds that contribute to the structure of the hair shaft.

A novel improvement in oxidation is available according to this invention. A combination of the TCEP and glucose is applied to the hair area where perming has taken place. The TCEP performs the reducing action while glucose molecules remain in the same vicinity. Then following reduction, the enzyme glucose oxidase is applied to the hair to complete the oxidation procedure precisely where the glucose and TCEP are located. Thus, an abundance of hydrogen peroxide is formed exactly where it is needed, at the site of the original reduction.

It is the preferred embodiment of this invention, and the best mode to incorporate the TCEP and glucose in a liposomal package in order to reduce the disulfide bonds and position glucose for subsequent oxidation of the sulfhydryl groups. Then, a second liposome, containing glucose oxidase is applied to the hair shaft which will react with the glucose previously deposited. There, and only there, will hydrogen peroxide be generated in situ to set disulfide bonds into a permanent condition. This reaction leads to localized concentrations of hydrogen peroxide where glucose is deposited and avoids the traditional pitfalls using commonly applied oxidizing agents where hydrogen peroxide is used in excess and puts the consumer at risk.

An example of the best mode and preferred embodiment procedure is:

Step 1) Dissolve 6.0 g of TCEP in 18.0 ml of deionized water in a 100 ml beaker. Place beaker in a cold water bath and adjust to pH 5.2 with a drop by drop addition of concentrated sodium hydroxide.

Step 2) Prepare a buffer solution by mixing 55.3 ml of 1.0M sodium acetate and 14.7 ml of 1.0M acetic acid in a total volume of 70.0 ml using deionized water.

Step 3) Bring the product of Step 1 up to approximately 50 ml by adding the product of Step 2. Also, add 210 mg of sodium chloride and 250 mg of sodium lauryl sulfate. Mix and bring the volume to 60.0 ml total with the product of Step 2.

Step 4) If a liposomal formulation is desired, add 1.75 ml of hydrogenated phosphatidyl choline (HSPC)[1] to the product of Step 3.

[1]To prepare 3% w/v HSPC, add 3 g of HSPC to approximately 100 ml of boiling distilled water. Then mix by polytroning for 5 minutes. Return the HSPC mixture to boiling and allow to cool to room temperature. Make final volume to 100 ml with distilled water.

Step 5) Microfluidize the product of Step 4 two times at ambient temperature at 7000 psig shear pressure using the Model 110 microfluidizer.

What is claimed is:

1. In a hair perming procedure, wherein said hair is structured by naturally occurring disulfide bonds, the procedure being to force the hair into the physical form that will establish the final hair set, thereafter chemically breaking the natural occurring disulfide bonds of the hair, and finally oxidizing the hair to create new disulfide bonds to set the hair into the new form, the improvement comprising:

the step of breaking the disulfide bonds with a reducing agent comprising TCEP in a mildly acidic environment, and to complete the reduction in about 10–15 minutes, the reducing agent being water soluble at about 300 g/L, and being odorless and non-volatile.

2. In the process of altering the physical configuration of hair, wherein the hair is forced out of a first configuration and into a second configuration and thereafter treated with a reducing agent to break the naturally occurring disulfide bonds of the hair, and finally restoring the disulfide bonds with an oxidizing agent, whereby the hair disulfide bonds holds the hair in its new condition; the improvement in the step of breaking the disulfide bonds is accomplished by application of TCEP to the hair.

3. A hair perming procedure, comprising:

mechanically stressing the hair into a configuration which will reflect the ultimate configuration;

thereafter applying a solution of TCEP to the stressed hair to reduce the natural disulfide bonds which give structural strength to the hair shaft, said hair treated with TCEP becoming limp and pliable as the reducing action takes place, and;

finally, applying an oxidizing media to said reduced hair to re-establish said disulfide bonds, thereby establishing said hair permanently in said altered configuration.

4. In a hair perming procedure wherein the hair is first stressed into a desired configuration, whereafter a reducing agent is applied to break disulfide bonds naturally occurring in the hair structure, and the bonds are re-established by an oxidizing agent, the improvement comprising:

a buffered solution of TCEP as the reducing agent applied in a mildly acid environment.

5. In a hair perming procedure, wherein an application of an oxidizing agent is an integral step in the procedure, the improvement in the procedure of breaking the naturally occurring disulfide bonds of the hair and thereafter restoring the bonds, comprising: applying TCEP and glucose together to break the bonds and prepare the environment for the local production of hydrogen peroxide, and after the forming steps of the hair perming procedure, applying glucose oxidase to the new environment; whereby, the glucose and the glucose oxidase react to produce hydrogen peroxide which will in turn react with reduced disulfide bonds to re-establish the bonds.

6. The procedure of claim 5, the further improvement of reduction and oxidation, comprising:

filling a first liposome with TCEP and glucose, and a second liposome with glucose oxidase, whereby the first liposome will break the disulfide bonds and hold the glucose at the location of bond reduction, and the second liposome is applied to react with the glucose to produce hydrogen peroxide.

* * * * *